United States Patent
Desarzens et al.

(10) Patent No.: US 7,572,259 B2
(45) Date of Patent: Aug. 11, 2009

(54) INSET ACETABULAR REAMER COUPLING

(75) Inventors: Yves Desarzens, Corgémont (CH); Hugh Davies, Huddersfield (GB); Patrick White, West Chester, PA (US); Andre Lechot, Orvin (CH)

(73) Assignee: Greatbatch Ltd., Clarence, NY (US)

( * ) Notice: Subject to any disclaimer, the term of this patent is extended or adjusted under 35 U.S.C. 154(b) by 0 days.

(21) Appl. No.: 10/526,683

(22) PCT Filed: Sep. 12, 2003

(86) PCT No.: PCT/IB03/04008

§ 371 (c)(1),
(2), (4) Date: Nov. 6, 2005

(87) PCT Pub. No.: WO2004/024007

PCT Pub. Date: Mar. 25, 2004

(65) Prior Publication Data

US 2006/0129157 A1      Jun. 15, 2006

Related U.S. Application Data

(60) Provisional application No. 60/411,236, filed on Sep. 16, 2002, provisional application No. 60/411,237, filed on Sep. 16, 2002.

(51) Int. Cl.
*A61B 17/00* (2006.01)
(52) U.S. Cl. ............................................ 606/81; 606/80
(58) Field of Classification Search ............. 606/79–81, 606/86, 91, 167–170, 172, 173; 623/16.11–23.63; 279/93, 19.5, 149; 408/203.5, 204, 239 R; 79/21, 50; 403/12, 17, 19; 81/177.1, 177.85
See application file for complete search history.

(56) References Cited

U.S. PATENT DOCUMENTS

| | | | | | |
|---|---|---|---|---|---|
| 3,412,733 | A | * | 11/1968 | Ross | 606/81 |
| 3,847,154 | A | * | 11/1974 | Nordin | 606/180 |
| 4,023,572 | A | | 5/1977 | Weigand et al. | |
| 5,176,711 | A | | 1/1993 | Grimes | |
| 5,203,653 | A | * | 4/1993 | Kudla | 408/207 |
| 5,376,092 | A | * | 12/1994 | Hein et al. | 606/81 |
| 5,658,290 | A | * | 8/1997 | Lechot | 606/80 |
| 5,879,355 | A | * | 3/1999 | Ullmark | 606/93 |
| 6,106,536 | A | * | 8/2000 | Lechot | 606/180 |
| 6,129,732 | A | * | 10/2000 | Lechot | 606/80 |

(Continued)

FOREIGN PATENT DOCUMENTS

DE        19532898        3/1997

(Continued)

OTHER PUBLICATIONS

International Search Report IN SN PCT/IB03/04008.

*Primary Examiner*—Eduardo C Robert
*Assistant Examiner*—Tara R George
(74) *Attorney, Agent, or Firm*—Michael F. Scalise

(57) ABSTRACT

An acetabular reamer for surgical use includes (a) a substantially hemispherical dome defining an equatorial plane, and (b) a reamer spindle interface structure fixedly attached to the inside of the dome so as to substantially inset the interface structure within the dome. This insetting of the interface structure helps minimize the size of an assembly of the reamer and a reamer spindle when performing minimally invasive joint surgery.

9 Claims, 5 Drawing Sheets

U.S. PATENT DOCUMENTS

| | | | |
|---|---|---|---|
| 6,250,858 B1 * | 6/2001 | Salyer | 408/239 R |
| 6,409,732 B1 * | 6/2002 | Salyer | 606/91 |
| 6,475,221 B1 * | 11/2002 | White et al. | 606/80 |
| 6,918,914 B2 * | 7/2005 | Bauer | 606/81 |
| 6,951,563 B2 * | 10/2005 | Wolford | 606/81 |
| 2002/0010470 A1 * | 1/2002 | Lechot | 606/80 |
| 2003/0130741 A1 * | 7/2003 | McMinn | 623/23.14 |
| 2003/0163135 A1 * | 8/2003 | Hathaway | 606/80 |
| 2003/0181916 A1 * | 9/2003 | Wolford | 606/81 |
| 2003/0216716 A1 * | 11/2003 | Desarzens | 606/1 |
| 2003/0229356 A1 * | 12/2003 | Dye | 606/99 |
| 2005/0203525 A1 * | 9/2005 | White et al. | 606/80 |
| 2006/0189994 A1 * | 8/2006 | Wolford et al. | 606/80 |

FOREIGN PATENT DOCUMENTS

| | | |
|---|---|---|
| EP | 0782840 A1 | 9/1997 |
| EP | 1 066 796 | 1/2001 |
| WO | WO 99/47051 | 9/1999 |
| WO | WO 01 76490 | 10/2001 |

* cited by examiner

INSET ACETABULAR REAMER COUPLING

This application is a 371 filing of PCT/IB2003/004008 filed Jul. 25, 2003 and published Mar. 25, 2004 under publication WO 2004/024007 and claims priority benefits of U.S. Patent Applications No. 60/411,236 and No. 60/411,237 both filed Sep. 16, 2002.

BACKGROUND OF THE INVENTION

Field of the Invention

This invention relates to mounting and insetting reamer couplings inside of acetabular reamer shells for the purpose of minimizing the size of the reamer and reamer coupling assembly when performing minimally invasive joint surgery.

Orthopedic surgeons have become quite familiar with using acetabular reamers for joint reconstructive surgery. In particular, most instrument sets available to the surgeons include modular acetabular reamer shells ranging anywhere from 36 mm to 80 mm in spherical diameter, this range of size being useful for reshaping the cotyloid cavity during hip surgery. These reamers are usually configured to mount on a reamer spindle with some type of coupling acting as the interface. An example of a typical coupling is shown in U.S. Pat. No. 5,658,290 to Lechot, in U.S. Pat. No. 4,023,572 to Weigand, and WO 99/47051 to Fishbein, the contents of which are incorporated by reference hereto. These predicate designs show various cross connectors, bayonet connectors as well as a single bar having a centering boss or hole. All of these couplings allow the modular reamer handle to be connected in a simple manner to the reamer so that the reamer and the handle are fixed together so that their interface is in close proximity to the center of the spherical portion of the reamer. Many of these designs have become the state of the art and can typically be found in use at surgical centers. Although these designs have been successful in the current market, market demand for minimally invasive surgery is increasing. This trend pressures surgeons to make much smaller incisions to access the femoral and acetabular cavities for reconstructive hip surgery, thus increasing demand for specialized instruments. Generally, smaller incisions result in much less blood loss and quicker patient recovery times, thus significantly improving surgical outcome both from the perspective of the patient and the insurance companies which pay for the recovery costs incurred as a result of these types of surgical procedures. The increased demand for minimally invasive surgery has in turn created an increased demand to decrease the size of instruments which are to be introduced into the patient and consequently has begun to substantially change the design of surgical instruments. One means of helping minimize the invasiveness of surgery is by reducing the size of the surgical reamer as proposed in the Lechot U.S. Pat. No. 6,106,536 patent entitled "Surgical reamer". This patent describes a portion of a sphere suspended from a cross connector on a shaft. While the designs of the Lechot '536 patent and other smaller profile reamers solve one aspect of the problem, there are other challenges faced by the surgeons while exercising this new technique. During surgery, the patient's femoral neck must be resected and the femoral bone disengaged from the acetabular socket. Because of the limited amount of room brought about by the smaller incision, it becomes much more difficult to position the femoral bone so as to provide the space necessary to ream the acetabular socket. As a result, the spindle of the reamer or shaft impinges either on the femoral bone or on the edge of the incision, thus making it difficult to properly prepare the cotyloid cavity. Others have sought to solve this problem of impingement by mounting a substantially hemispherical shell of the prior art onto a fixed angled reamer driver. However, the mechanism in the driver still impinged on the bone during cutting.

What is needed therefore is a surgical reamer assembly that reduces impingement on the femoral bone as well as the size of the incision during minimally invasive joint surgery. Further, what is needed is a surgical reamer with a connector that is compatible with existing instrumentation and can be used universally for both minimally invasive surgical approaches and traditional surgical approaches.

BRIEF DESCRIPTION OF DRAWINGS

The attached drawings represent, by way of example, different embodiments of the subject of the invention.

DETAILED DESCRIPTION OF DRAWINGS

Figure 1:
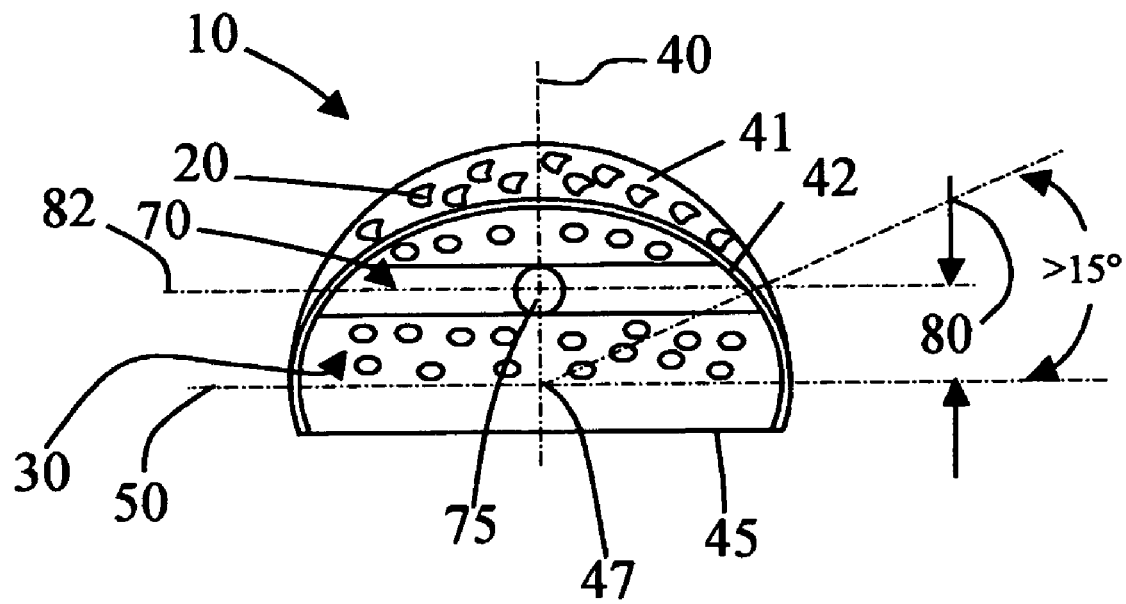
FIG. 1 is a side view of the preferred inset reamer cross coupling of the present invention.
Figure 2:
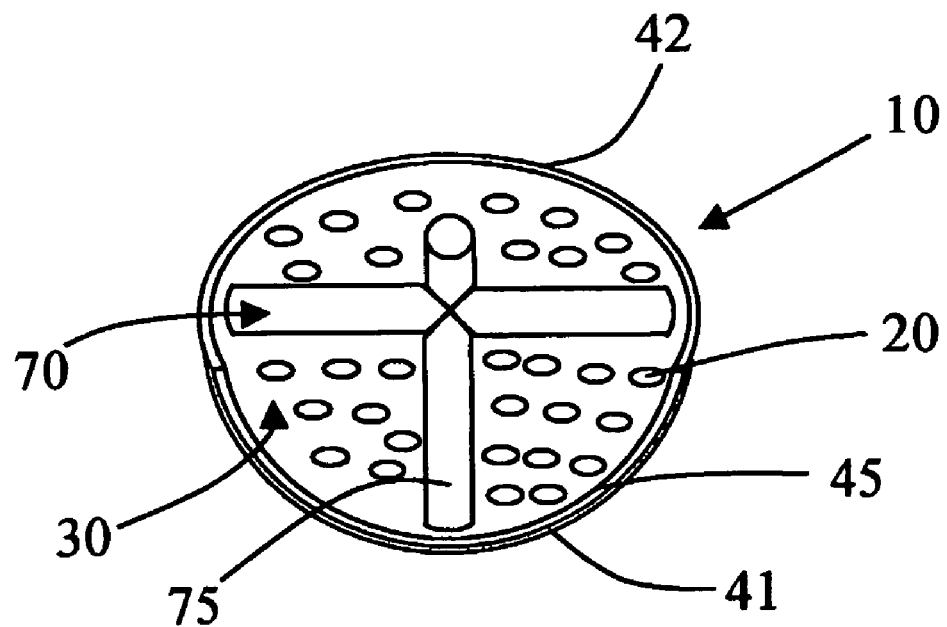
FIG. 2 is a bottom view of the preferred inset reamer cross coupling of the present invention.

Referring now to FIGS. 1-2, a hollow acetabular reamer 10 for surgical use is shown. The reamer 10 includes a substantially hemispherical hollow dome or shell defining a rotational axis 40, an equatorial plane 50 (i.e., the plane comprising the equator and intersecting the rotational axis 40 at the center 47 of the sphere 41) and an apex. The acetabular reamer 10 has apertures 20 through the shell allowing reamed tissue and debris to pass into the central cavity 30 during cutting. The reamer 10 has a rotational axis 40 and is formed as a portion of a sphere 41 having a first cutaway side 42 and a second cutaway side 45. As described by one of the present inventors in the Lechot '536 patent, the first cut away side 42 allows the static insertion profile of the reamer 10 to be smaller than the dynamic profile and thus, when statically inserting the reamer through an incision, the reamer passes through the incision without as much tissue damage as would take place if the portion of the sphere were not removed.

A reamer spindle interface structure or connector 70 is fixedly attached to the inside of the dome at a junction located to substantially inset the interface structure within the dome. This insetting of the interface structure 70 helps minimize the size of an assembly of the reamer 10 and a reamer spindle 500, 600 (shown in FIGS. 9 and 10) when performing minimally invasive joint surgery.

In rotation about the axis 40, the reamer shell 10 sweeps a hemispherical volume defining a dynamic profile (i.e., the cutting profile). Although it is common for the second side 45 to be coincident to the equatorial plane 50, optionally, it can be offset angularly or manufactured parallel to it as shown in FIG. 1. An interface structure or connector in the form of a cross 70 is mounted to the inside of the central cavity 30. The cross 70 is formed from radial spokes 75 and is the structure that acts as an interface between the sphere 41 and the handle (not shown). The cross 70 is substantially inset from the hemispherical plane (i.e., equator) 50 by a set distance 80 into the central cavity 30 of the reamer shell 10. The latitudinal plane 82, along which the radial spokes 75 are located, is at least 15 degrees from the equator 50 of the hemisphere.

Figure 3:
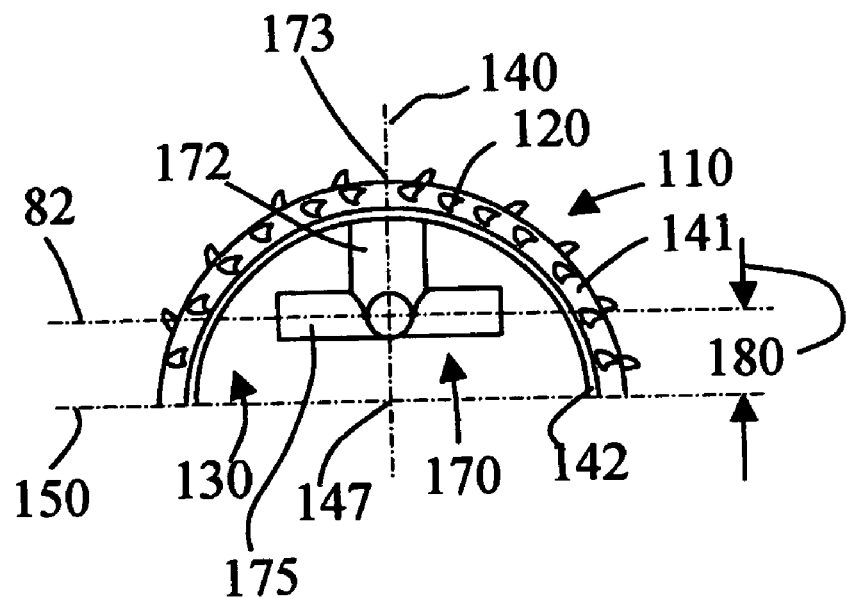
FIG. 3 is a side view of an inset reamer cross coupling mounted on a central post.
Figure 4:
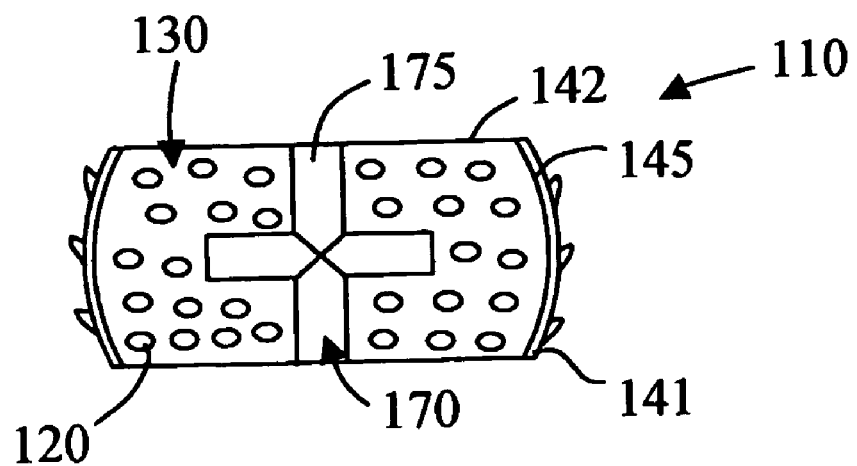
FIG. 4 is a bottom view of the inset reamer coupling shown in FIG. 3.

Referring now to FIGS. 3-4, a second embodiment of a hollow acetabular reamer shell 110 is shown with apertures 120 allowing reamed tissue and debris to move into the central cavity 130 during use. The shell 110 has a rotational axis 140 and is formed as a portion of a sphere 141 having two cutaway sides 142 and a rim 145. In rotation about the axis 140, the reamer shell 110 has a hemispherical plane 150 which intersects the axis at the center 147 of the sphere 141. It is common, as shown, for the rim 145 to be coincident to the hemispherical plane 150. A connector in the form of a cross 170 is mounted on a shaft 172 coincident with the axis 140 and is attached to the central cavity 130 near the apex 173. The cross 170 is formed from radial spokes 175 and acts as an interface between the sphere 141 and the handle (not shown). The cross 170 is substantially inset from the hemispherical plane 150 by a distance 180 into the central cavity 130 of the reamer shell 110. Note that here again, the two cutaway sides 142 contribute to further reducing the invasiveness of surgery using this device in a manner similar to the cutaway side 42 in the prior embodiment.

Figure 5:
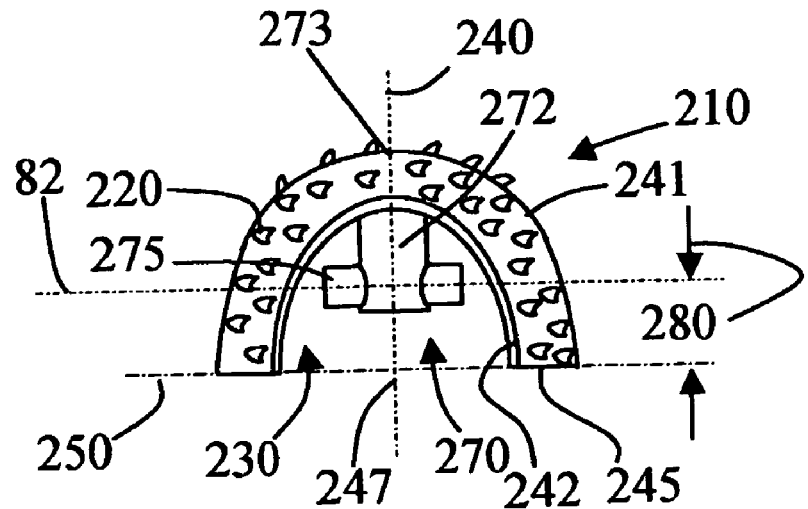
FIG. 5 is a side view of an inset bayonet reamer coupling.
Figure 6:
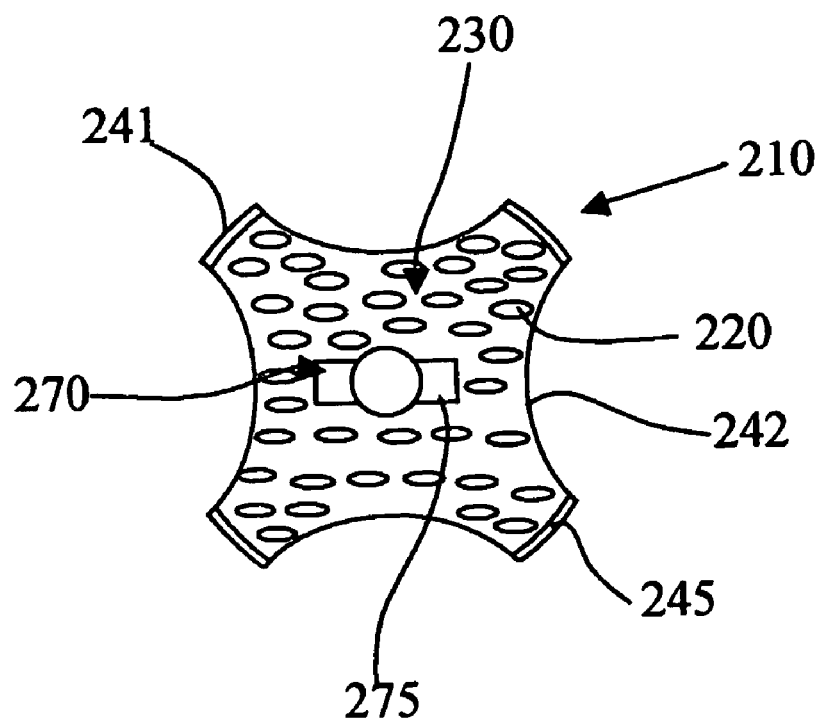
FIG. 6 is bottom view of the inset reamer coupling shown in FIG. 5.

Referring now to FIGS. 5-6, a third embodiment of the hollow acetabular reamer shell 210 is shown with apertures 220 allowing reamed tissue and debris to pass into the central cavity 230 during cutting. The shell 210 has a rotational axis 240 and is formed as a portion of a sphere 241 having curved cutaway sides 242 (thus reducing invasiveness) and a rim 245. In rotation about the axis 240, the reamer shell 210 has a hemispherical plane 250 which intersects the axis at the center 247 of the sphere 241. It is common, as shown, for the rim 245 to be coincident to the hemispherical plane 250. A connector in the form of a bayonet 270 is mounted on a shaft 272 which is coincident with the axis 240 and is attached to the central cavity 230 near the apex 273. The bayonet 270 is formed from two radial spokes 275 and acts as an interface between the sphere 241 and the handle (not shown). The bayonet 270 is substantially inset from the hemispherical plane 250 by a distance 280 into the central cavity 230 of the reamer shell 210.

Figure 7:
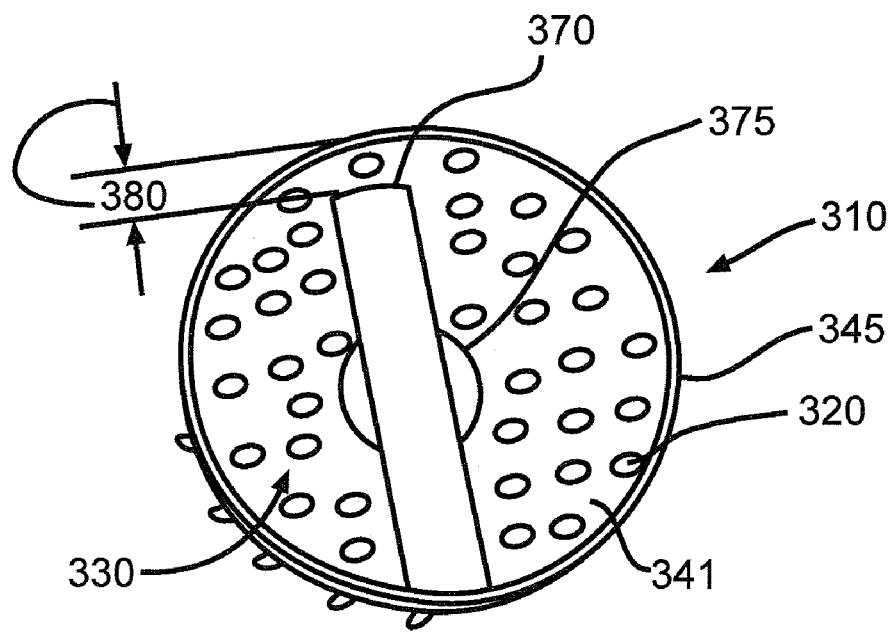
FIG. 7 is an isometric view of a reamer coupling having an inset bar with a boss.

Referring now to FIG. 7, a fourth embodiment of the hollow acetabular reamer shell 310 is shown with apertures 320 allowing reamed tissue and debris to pass into the central cavity 330 during cutting. The shell is formed as a hemisphere 341 having a rim 345. A connector in the form of a unitary bar 370 with a central embossed portion 375 is mounted to the inside of the central cavity 330. The bar 370 acts as an interface between the sphere 341 and the handle (not shown). The unitary bar 370 is substantially inset from the hemispherical rim 345 as illustrated by dimension 380.

Figure 8:
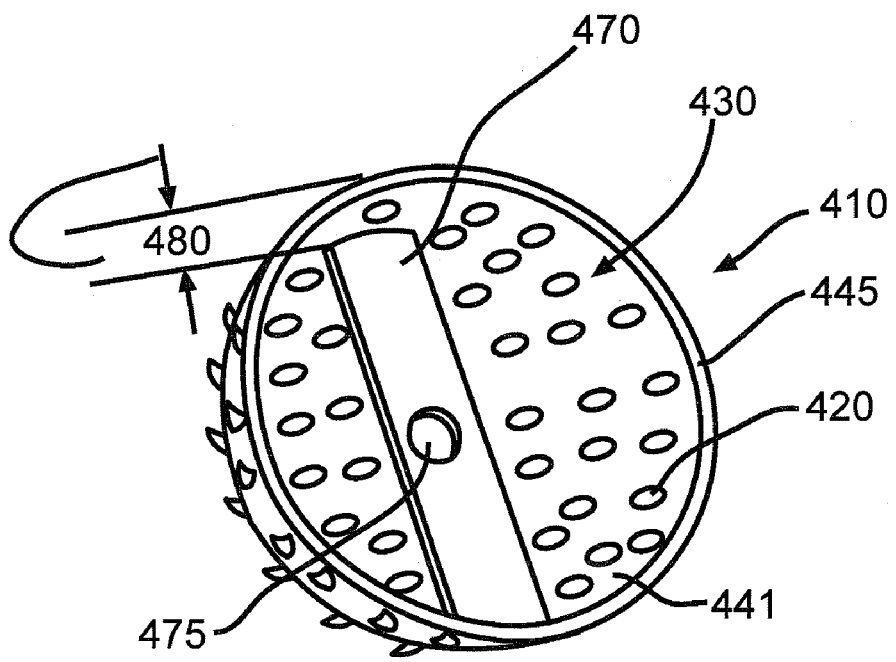
FIG. 8 is an isometric view of a reamer coupling having an inset bar with a centralizing hole.

Referring now to FIG. 8, a fifth embodiment of the hollow acetabular reamer shell 410 is shown with apertures 420 allowing reamed tissue and debris to pass into the central cavity 430 during cutting. The shell is formed as a hemisphere 441 having a rim 445. A connector in the form of a unitary bar 470 has a central alignment hole 475. The connector is mounted to the inside of the central cavity 430 and acts as an interface between the sphere 441 and the handle (not shown). The unitary bar 470 is substantially inset from the hemispherical rim 445 as illustrated by dimension 480.

Figure 9:
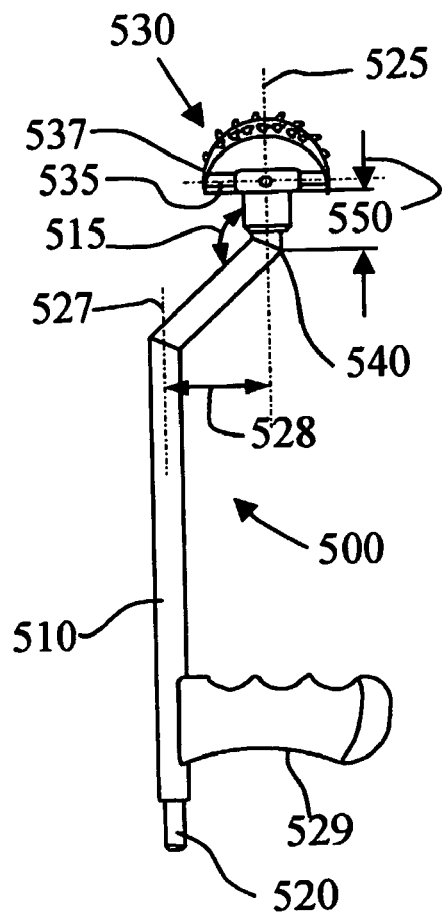
FIG. 9 is a side view of a reamer coupling of the prior art mounted on a minimally invasive reamer handle.

FIG. 9 generally shows an instrument assembly 500 having an angled reamer spindle 510 which has at least one angular offset 515 to reorient the driven end 520 off the rotational axis 525 for the purpose of avoiding soft tissue and bone impingement during reaming of the cotyloid cavity. The spindle 510 has a drive axis 527 parallel to the rotational axis 525 and offset by a distance 528. The assembly 500 is equipped with a grip 529 for guiding the reamer along the rotational axis 525 during use. The reamer spindle 510 is coupled in a fixed relative position to a spherical reamer 530 to form the assembly 500. Assemblies 500 of this type have been used in surgery and have realized vast improvement over straight spindle assemblies insofar as reducing soft tissue impingement is concerned.

When the driven end 520 is turned by a source of rotary power, the reamer 530 turns, thereby allowing the surgeon to transmit torque to affect the bone cut. The spherical reamer 530 is shown with a cross coupling 535 mounted through the hemispherical plane passing generally through the center of the reamer 530 and is useful for coupling the reamer to the spindle 510. The reamer 530 has a portion of a sphere which has been removed by cutting away a side 537 to create a low profile reamer 530 as described above in prior embodiments. Thus, when used with an angled reamer spindle 510, the surgeon gains multiple benefits. These improvements have proven quite successful. Nevertheless, due to different emerging surgical protocols, problems with bone impingement still exist using this assembly 500. In particular, the bend point 540 still impinges the bone. In an effort to avoid impingement, the reamer spindle 510 was shortened; however, mechanical constraints do no allow the assembly to become any shorter. In particular, the front portion can only be reduced to somewhere between 30 mm and 45 mm, depending on the design.

Figure 10:
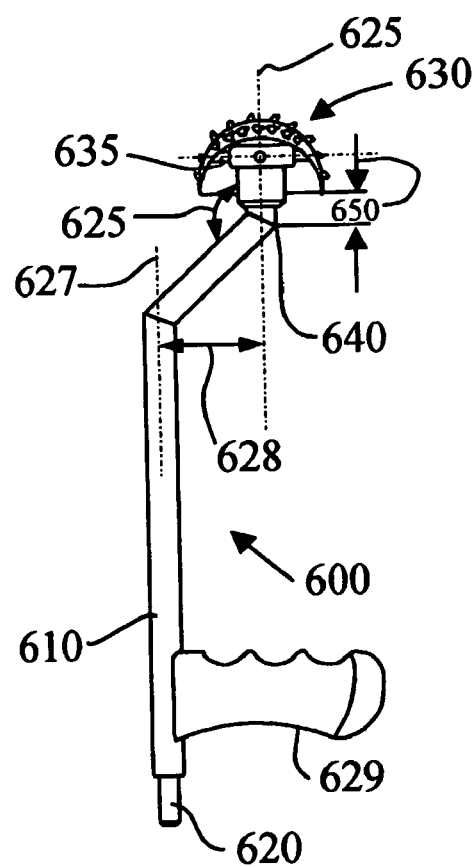
FIG. 10 is a side view of a reamer coupling of the present invention mounted on a minimally invasive reamer handle.

Therefore, referring now to FIG. 10, the mechanical constraint is shown to be reduced by substantially insetting the coupling into the reamer shell as depicted by dimension 550. FIG. 10 generally shows an instrument assembly 600 having an angled reamer spindle 610 which has at least one angular offset 615 which reorients the driven end 620 off the rotational axis 625 for the purpose of avoiding soft tissue and bone impingement during reaming of the cotyloid cavity while performing minimally invasive joint surgery. The spindle 610 has a drive axis 627 parallel to the rotational axis 625 and offset by a distance 628. It is equipped with a grip 629 for guiding the reamer along the rotational axis 625 during use. The reamer spindle 610 is coupled in a fixed relative position to a spherical reamer 630 to form the assembly 600. When the driven end 620 is turned by a source of rotary power, the reamer 630 turns, thereby allowing the surgeon to transmit torque in order to effectively cut the bone. The spherical reamer 630 is specifically shown with a cross coupling 635 substantially inset into the reamer as shown in FIGS. 1-2 at 80 and can be substituted more generally with other spherical reamers that present alternative inset couplings such as those shown in FIGS. 3-8 at 180, 280, 380 and 480. Assemblies 600 of this type solve the impingement issues faced by the surgeon in all surgical protocols. Further, when used with a low profile reamer 630, the surgeon gains multiple benefits. These improvements have proven quite successful and, compared to the assembly 500 shown in FIG. 9, the bend point 640 has a dimension 650 which is much shorter and closer in to the shell. Therefore, effectively, the dimension 650 is somewhere between 5 mm to 35 mm shorter than dimension 550 from the prior art coupling. Any bend configuration of the spindle can be used as a substitute for the spindle 510 and 610 shown in these embodiments. In particular, all spindles described in the incorporated applications U.S. 60/376,479 entitled "Reamer Spindle for Minimally Invasive Joint Surgery" and U.S. 60/384,186 entitled "Easy Clean Minimally Invasive Surgical Reamer" are preferred substitutions for the reamer spindles 510 and 610. These spindles 510 and 610 are disclosed to further illustrate the offset parallel spindle embodiment described in application 60/384,186, but not shown here.

The benefits of substantially insetting a coupling which interlocks in a fixed relative position with a spindle can be applied to all types of hollow shell acetabular reamers whether or not they have a small profile. In fact, multiple variations and modifications are possible in the embodiments of the invention described here. Although certain illustrative embodiments of the invention have been shown and describe here, a wide range of modifications, changes, and substitutions is contemplated in the foregoing disclosure. In some instances, some features of the present invention may be employed without a corresponding use of the other features. Accordingly, it is appropriate that the foregoing description be construed broadly and understood as being given by way of illustration and example only, the spirit and scope of the invention being limited only by the claims, without prejudice to the amendments made during prosecution.

What is claimed is:

1. An acetabular reamer for surgical use, the reamer comprising:
   (a) a hemispherical, hollow dome extending from an apex to a lower edge defining a plane at a theoretical equator of the hemispherical dome; and
   (b) an interface structure comprising a shaft having a proximal end secured to an inner surface of the dome at the apex and extending to a distal end supporting at least two radial spokes extending therefrom in a radial spokes plane within the dome at an intermediate location between the theoretical equatorial plane of the hemispherical dome and the apex, wherein each radial spoke has a proximal end attached to the shaft and a distal spoke end spaced from an inner surface of the dome along the radial spokes plane.

2. The acetabular reamer of claim 1 wherein the interface structure comprises four radial spokes extending from the distal end of the shaft along the radial spoke plane.

3. The acetabular reamer of claim 2 wherein the four radial spokes are disposed at 90° with respect to each other.

4. The acetabular reamer of claim 1 wherein the radial spokes plane is parallel to the equatorial plane so that the interface structure is completely within the dome.

5. The acetabular reamer of claim 1 wherein the dome has at least one substantial section removed so as to reduce a static insertion profile of the reamer, as compared to a dynamic profile, in order to facilitate surgery which is relatively less invasive than a surgery performed with a comparable reamer not having the removed section.

6. The acetabular reamer of claim 1 wherein a plurality of sections of the dome are removed so as to reduce a static insertion profile of the reamer in order to permit surgery which is relatively less invasive than a surgery performed with a comparable reamer not having the removed sections.

7. The acetabular reamer of claim 5 wherein the removed sections are equally spaced about the equator of the dome.

8. The acetabular reamer of claim 5 wherein the section renders the dome asymmetrical.

9. A surgical reamer assembly, which comprises:
   (a) a hemispherical, hollow dome extending from an apex to a lower edge defining a plane at a theoretical equator of the hemispherical dome;
   (b) an interface structure comprising a shaft having a proximal end secured to an inner surface of the dome at the apex and extending to a distal end supporting at least two radial spokes extending therefrom in a radial spokes plane parallel to the equatorial plane so that the interface structure is completely within the dome at an intermediate location between the theoretical equatorial plane of the hemispherical dome and the apex, wherein each radial spoke has a proximal end attached to the shaft and a distal spoke end spaced from an inner surface of the dome along the radial spokes plane; and
   (c) an angled reamer spindle having a coupling, wherein the reamer and the spindle are detachably attachable to each other via the inset interface structure and the coupling, the assembly providing for comparably minimum invasiveness of orthopedic surgery.

* * * * *